(12) United States Patent
Jackson et al.

(10) Patent No.: US 7,695,439 B2
(45) Date of Patent: Apr. 13, 2010

(54) AUTOMATED IDENTIFICATION OF CARDIAC EVENTS WITH MEDICAL ULTRASOUND

(75) Inventors: John I. Jackson, Menlo Park, CA (US); Lei Sui, Renton, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1148 days.

(21) Appl. No.: 11/210,212

(22) Filed: Aug. 22, 2005

(65) Prior Publication Data

US 2007/0055158 A1    Mar. 8, 2007

(51) Int. Cl.
*A61B 8/00*    (2006.01)
(52) U.S. Cl. ..................................... 600/450
(58) Field of Classification Search ................. 600/450, 600/458, 437, 439, 451, 453, 498, 509
See application file for complete search history.

(56) References Cited

U.S. PATENT DOCUMENTS

| | | | | |
|---|---|---|---|---|
| 4,967,757 | A * | 11/1990 | Frankenreiter | 600/495 |
| 5,935,074 | A * | 8/1999 | Mo et al. | 600/454 |
| 5,997,883 | A * | 12/1999 | Epstein et al. | 324/306 |
| 6,193,660 | B1 | 2/2001 | Jackson et al. | |
| 6,258,029 | B1 | 7/2001 | Guracar et al. | |
| 6,527,717 | B1 | 3/2003 | Jackson et al. | |
| 6,579,238 | B1 | 6/2003 | Simopoulos et al. | |
| 6,607,488 | B1 | 8/2003 | Jackson et al. | |
| 6,612,992 | B1 | 9/2003 | Hossack et al. | |
| 6,628,743 | B1 * | 9/2003 | Drummond et al. | 378/8 |
| 6,645,147 | B1 | 11/2003 | Jackson et al. | |
| 6,673,017 | B1 | 1/2004 | Jackson | |
| 7,065,400 | B2 * | 6/2006 | Schechter | 607/2 |
| 2003/0013962 | A1 * | 1/2003 | Bjaerum et al. | 600/443 |
| 2004/0249259 | A1 * | 12/2004 | Heimdal et al. | 600/407 |
| 2004/0249314 | A1 * | 12/2004 | Salla et al. | 600/595 |
| 2004/0254467 | A1 | 12/2004 | Jackson | |
| 2005/0234340 | A1 * | 10/2005 | Brock-Fisher et al. | 600/458 |
| 2006/0058673 | A1 * | 3/2006 | Aase et al. | 600/450 |
| 2006/0122512 | A1 * | 6/2006 | Abe | 600/454 |
| 2007/0043294 | A1 * | 2/2007 | Li | 600/455 |

* cited by examiner

*Primary Examiner*—Eric F Winakur
*Assistant Examiner*—Lawrence N Laryea

(57) ABSTRACT

Automated analysis of ultrasound data is provided to extract event times, such as valve opening and closing times. Different types of ultrasound data, such as B-mode, M-mode, tissue velocity or flow velocity, are processed by a processor to identify automatically the event times. The event times are used for the processing of ultrasound data or to assist diagnosis. The event times may be used to estimate other event times in different heart cycles, such as with interpolation or extrapolation.

17 Claims, 3 Drawing Sheets

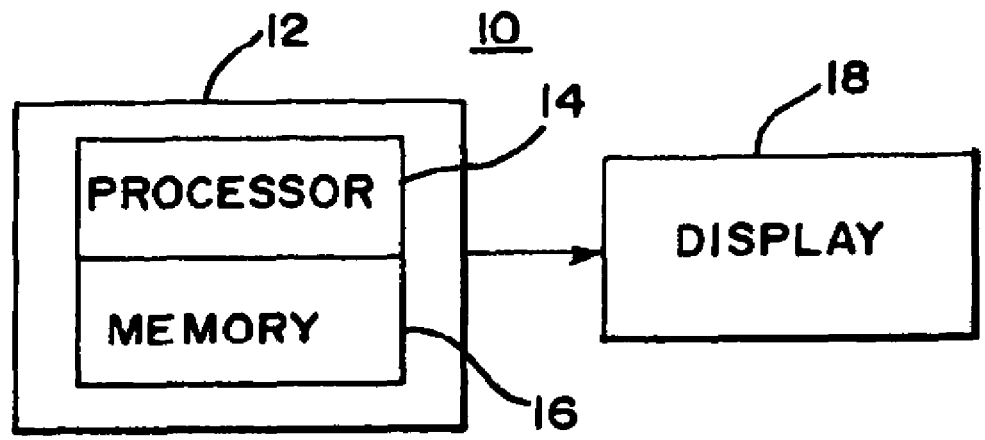
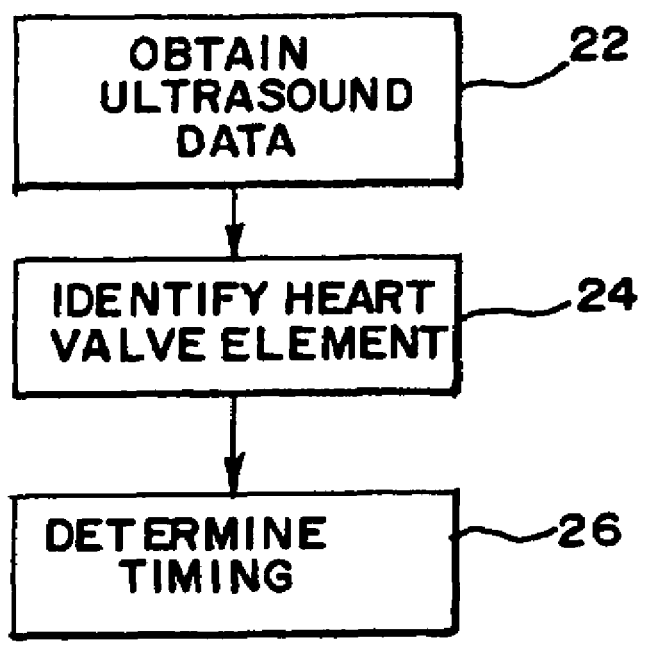

AUTOMATICALLY EXTRACTED AV TIMES
AVO @ R+33ms, AVC @ R+316 ms

AUTOMATED IDENTIFICATION OF CARDIAC EVENTS WITH MEDICAL ULTRASOUND

BACKGROUND

The present embodiments relate to identification of cardiac events. In particular, heart valve opening and/or closing is identified.

Heart valve opening and/or closing times may have diagnostic significance. To identify heart valve timing, the valve opening and closing times are manually measured, typically using ultrasound data. For example, the user positions a caliper marker along an ECG trace displayed adjacent to an ultrasound M-mode or spectral Doppler (PW or CW) image. The user identifies the opening and closing times by selecting the appropriate times on the ECG trace. The imaging system indicates the selected times as a caliper output. The manually identified and selected times are then either written down or entered into a database of patient measurements. If subsequent components of the patient exam require these times, the times are manually or automatically recalled and used. These manual time measurements may be time consuming and inconvenient.

BRIEF SUMMARY

By way of introduction, the preferred embodiments described below include methods, instructions and systems for automated analysis of ultrasound data to extract event times, such as valve opening and closing times. Different types of ultrasound data, such as B-mode, M-mode, tissue velocity or flow velocity, are processed by a processor to identify automatically the event times. The event times are used for the processing of ultrasound data or to assist diagnosis. The event times may be used to estimate other event times in different heart cycles, such as with interpolation or extrapolation.

In a first aspect, a method is provided for automated identification of a cardiac event. Ultrasound data responsive to a heart valve is obtained. A processor identifies an opening, closing or both opening and closing of the heart valve as a function of the ultrasound data.

In a second aspect, a system is provided for automated identification of a cardiac event. A memory is operable to store ultrasound data responsive to a heart valve. A processor is operable to identify heart valve motion with the ultrasound data.

In a third aspect, a method is provided for automated identification of a cardiac event. A first cardiac event time relative to a first heart cycle length is obtained. A second cardiac event time relative to a second heart cycle length is interpolated or extrapolated as a function of the first cardiac cycle time, the first heart cycle length and the second heart cycle length.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

FIG. 1 is a block diagram of one embodiment of a system for automated identification of a cardiac event;

FIG. 2 is a flow chart of one embodiment of a method for automated identification of a cardiac event;

DETAILED DESCRIPTION OF THE DRAWINGS AND PRESENTLY PREFERRED EMBODIMENTS

Figure 3:
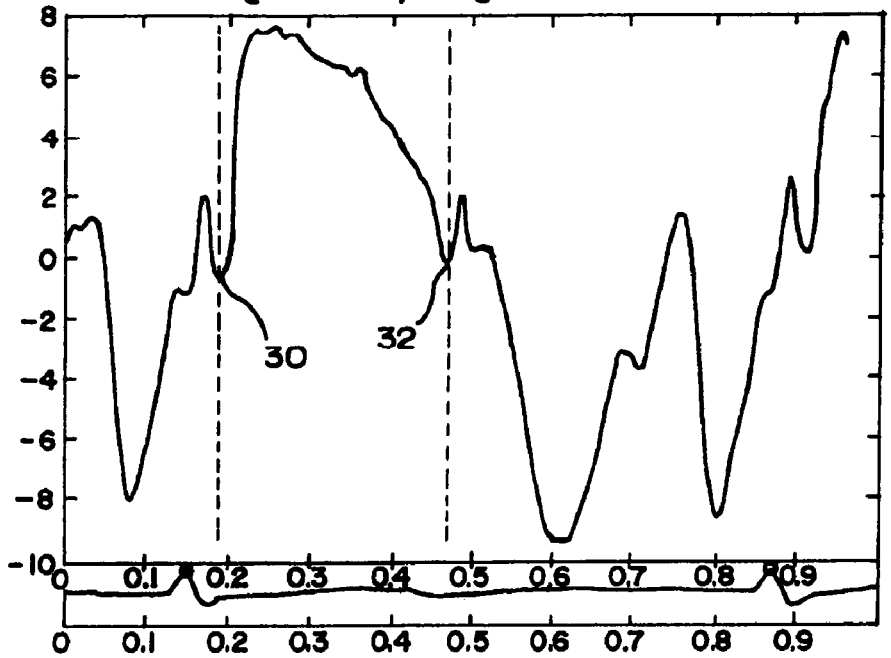
FIG. 3 is a graphical representation of one example of velocity as a function of time associated with a cardiac event.

Cardiac resynchronization therapy and strain rate analysis contribute to complex analysis of myocardial function. Intelligent algorithms may significantly reduce the time and effort required to derive the appropriate information from medical images for complex analysis. The extraction of the opening and closing times of the heart valves is important and time consuming when performed manually. By automating identification of heart valve events, more efficient examination or diagnosis may be provided. The heart valve event information may be intrinsically useful and displayed or included in a patient report. For use in cardiac analysis, the automatically determined heart valve events provide an appropriate time window to use to assess systolic cardiac synchrony, the automatic identification of post-systolic contraction associated with ischemia or other analysis of medical images.

A table of cardiac event times may be generated covering a range of R-R intervals. The table is used to predict, such as based on interpolation or extrapolation, event times at new R-R intervals. The predication allows for further assistance of image analysis or diagnosis.

FIG. 1 shows a system 10 for automated identification of cardiac events. The system 10 includes an imaging system 12 with a processor 14 and a memory 16, and a display 18. Additional, different or fewer components may be provided. For example, a transducer and beamformers connect with the processor 14. In one embodiment, the system 10 is a medical diagnostic ultrasound imaging system. Other medical (e.g., MRI, CT, x-ray, or PET) or non-medical imaging systems may be used. In another embodiment, the system 10 is a computer, workstation, laptop or other data processing device for processing stored or transferred data.

The memory 16 is video random access memory, random access memory, removable media (e.g. diskette or compact disc), optical memory, magnetic memory, hard drive, database, corner turning memory, cache or other memory device for storing data or video information. In one embodiment, the memory 16 is a system memory for access by the processor 14. The memory 16 is operable to store ultrasound or other medical data formatted in an acoustic grid, a Cartesian grid, both a Cartesian coordinate grid and an acoustic grid, or ultrasound data representing a volume in a 3D grid. Different frames of data, images or portions of images are associated with different times, such as different absolute times, relative times or times with respect to a heart cycle. The different times are stored with the data, such as in a header. The memory 16 or a different memory stores instructions for operation of the processor 14 or other devices in the imaging system 12.

The memory 16 is operable to store ultrasound or other medical data responsive to a heart valve. The data represents a single image, multiple images, a sequence of images, a parameter as a function of time and/or space, or other information. Image data includes data not yet displayed or even not yet formatted for display. For ultrasound data, the data responsive to the heart valve is acquired using any of various imaging modes, such as B-mode images, an M-mode strip image, a spectral Doppler strip, tissue velocity images, fluid velocity images, or combinations thereof. Valve opening and closing times can be extracted from various modes of imaging. For example, a pattern change along the beam line or logical line is identified from an M-mode image. As another example, a pattern change in the region of the valve is identified from 2D or 3D B-mode clips. As yet another example, a characteristic change in the velocity of the basal septum occurs with aortic valve opening and closing in tissue Doppler velocity images. As another example, the onset of cessation of flow in the vicinity of the appropriate valve indicates valve opening and closing in color Doppler Velocity images (i.e., fluid flow velocity) or in PW or CW Doppler images (i.e., spectral Doppler).

The processor 14 is one or more general processors, control processors, application-specific integrated circuits, field-programmable gate arrays, digital circuits, analog circuits, digital signal processors, combinations thereof, or other now known or later developed devices for identifying cardiac events from data. The memory 16 connects with the processor 14 for accessing data for or during automatic analysis by the processor 14. The functions, acts or tasks illustrated in the figures or described herein are performed by the processor 14 executing instructions stored in or on computer-readable storage media.

The processor 14 identifies heart valve motion with the ultrasound data. For example, the processor 14 determines an amount of correlation or pattern match between the ultrasound data as a function of time. As another example, the processor 14 identifies the motion as a function of a parameter variation as a function of time. The process is automatic, such as being performed without user intervention or changes once initiated. User input may be used in the process. For example, the user indicates a region, volume, area, line or point of interest associated with one or more heart valves. As another example, the user indicates an identity of a heart valve. The user indication is direct, such as by selecting a type of heart valve, or indirect, such as inferring the type of heart valve from the user making specific manual measurements on an image or selecting certain imaging presets. The processor 14 operates differently to identify cardiac events depending on the type of heart valve.

The processor 14 selects an algorithm for identifying heart valve motion, such as opening and/or closing events. Other data to be used by the algorithm is obtained, such as a region of interest being obtained by user indication and/or tracking. The data for analysis is obtained, such as selecting a clip of images or a strip. A subset of the data may be used, such as limiting a search for a cardiac event to approximate time intervals. For example, if the user measures the peak velocity of an aortic stenosis jet, the analysis searches the data for the start and end of the flow towards the transducer starting soon after the R-wave and ending roughly 300-400 ms after the R-wave.

The processor 14 identifies the cardiac events as a function of the type of data available. For example, a sequence of tissue velocity data (e.g., tissue Doppler velocity) is available, such as associated with strain rate imaging. The data represents the aortic or other valve, such as being associated with scanning the basal septum. FIG. 3 shows an average velocity for a region of interest corresponding to the basal septum. A median or other function may be used. The velocity of other regions, such as the heart valve may be used. The valve opening time corresponds to a notch 30 with a velocity near zero soon after the R-wave or negative peak. The ECG is shown by a small graph at the bottom of FIG. 3, and the R-waves are indicated by the large bumps in that graph. Small circles have been placed on top of these bumps to indicate the location of the peak of each R-wave. The valve closing time corresponds to a notch 32 with a velocity near zero after a large positive peak and/or in the 250 ms-400 ms range after the R-wave. The algorithm identifies these notches 30, 32. In another approach, the algorithm locates the maximum positive peak in a given heart cycle and then identifies the first sufficiently large notches 30, 32 before and after the maximum positive peak. Other approaches may be used.

Figure 4:
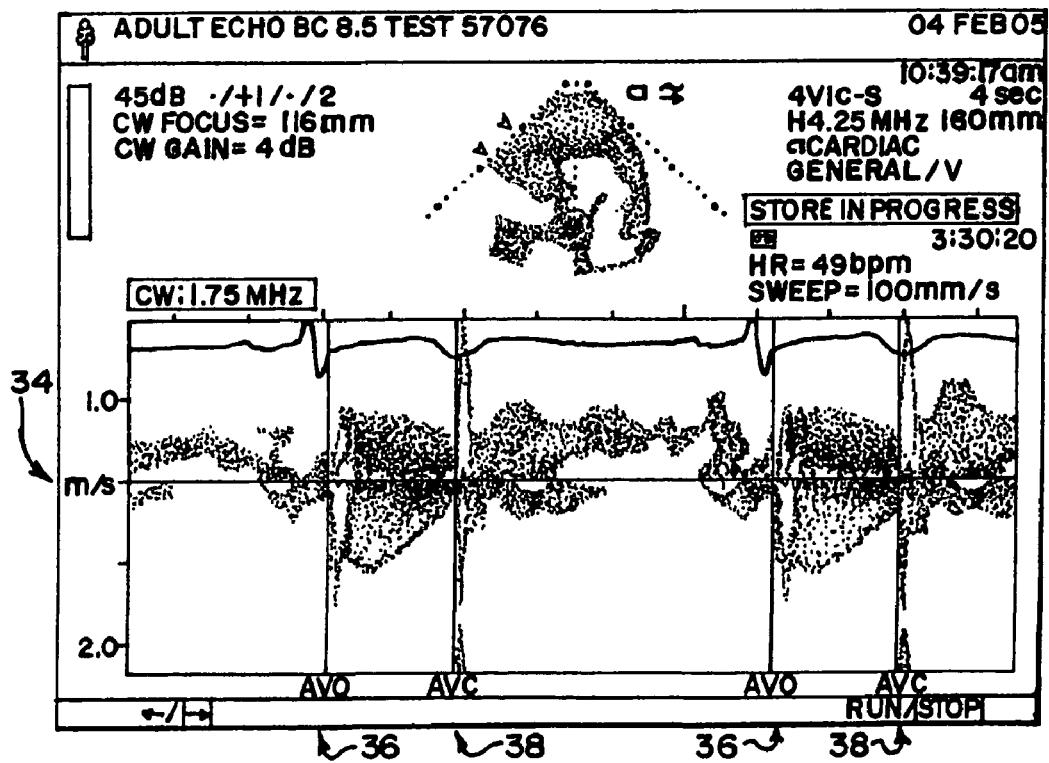
FIG. 4 is a graphical representation of one example of continuous wave ultrasound data associated with a cardiac event.

As another example, the available data is continuous wave (CW) or pulsed wave (PW) Doppler (e.g., spectral Doppler) data. FIG. 4 shows one example of a strip 34 of CW Doppler data. The range gate location is positioned at the valve, such as the aortic valve. The envelope of the flow is determined, such as by applying a threshold, filtering and/or other process. The local minima near the beginning and ending of a continuous outflow are identified from the envelope as the opening 36 and closing 38 of the valve. The largest negative peak of the envelope in a heart cycle is located. The first sufficiently large notches and/or approach of the envelope to zero values indicate the opening 36 and closing 38 of the valve. Other approaches may be used, such as identifying locations relative to valve clicks.

Figure 5:
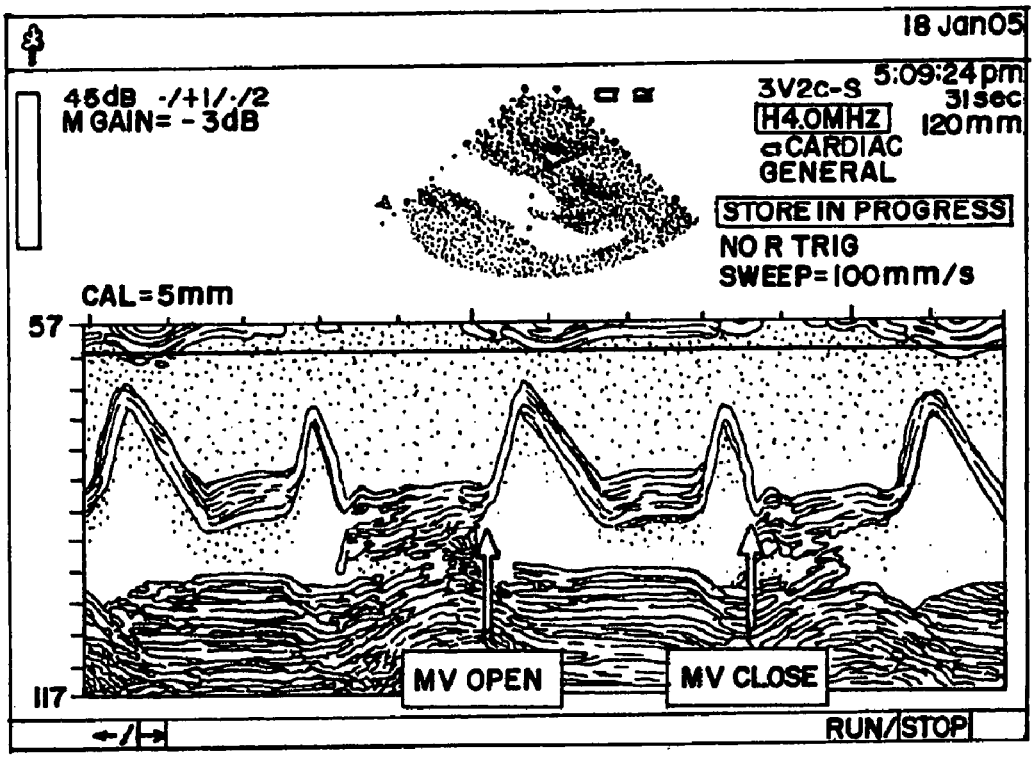
FIG. 5 is a graphical representation of one example of M-mode ultrasound data associated with a cardiac event.
Figure 6:
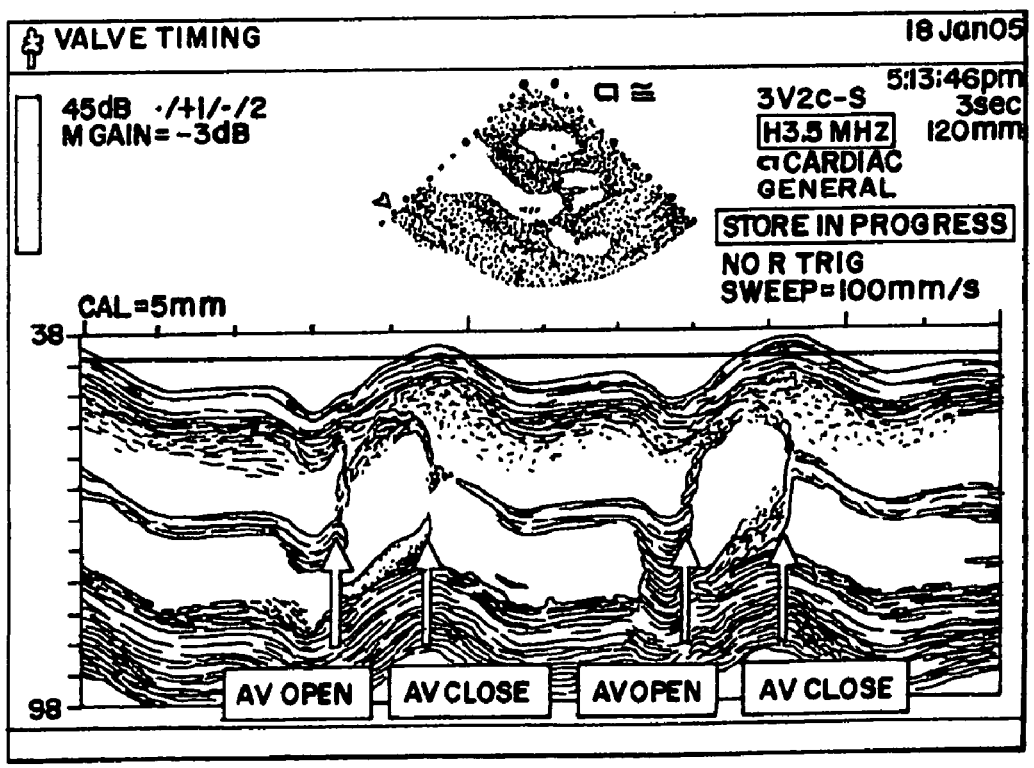
FIG. 6 is a graphical representation of another example of M-mode ultrasound data associated with a cardiac event.

As yet another example, the available data is M-mode data. FIGS. 5 and 6 show M-mode strips over multiple heart cycles. FIG. 5 shows a PLAX view base M-mode strip of the mitral valve. FIG. 6 shows a PLAX view based M-mode strip of the aortic valve. In one embodiment, the opening and closing events are identified by matching a pattern representing a heart cycle or portion of the M-mode image associated with opening and closing to the data. In another embodiment, the opening and closing events are identified in FIG. 5 by locating variation in location of sufficiently strong tissue response closest to the transducer. The user or the processor 14 may mask the M-mode strip to exclude tissue outside of the heart. The rapid movement of the tissue closer to the transducer represents opening of the valve, and the end of rapid movement away from the transducer after a subsequent further movement towards the transducer represents closing of the valve. In yet another embodiment, the opening and closing events are identified in FIG. 6 by applying circular filtering to the M-mode strip. The leftmost and rightmost edges of the resulting circular features indicate the opening and closing of the valve. Other approaches may be used.

As yet another example, the available data is B-mode data. A region of interest corresponding to a line or area passing from one chamber to another chamber through a valve is designated by the processor 14 or the user. For example, a line is positioned through the mitral valve in a two-dimensional B-mode image. The line is maintained in a same position throughout a clip, tracked by the processor 14 and/or manually positioned through the clip or sequence of images. The intensities along the line are extracted for each of the images. An amount of correlation of the intensities along the line with intensities along the line in a subsequent image is calculated. The calculation is repeated as a function of images or time. A threshold is applied to the amount of correlation through the sequence. Any level of correlation may be selected, such as 40 or 60%. The threshold is static or dynamic, such as being adaptive based on a level of inter-image variance. In one embodiment, Otsu thresholding is applied. Any correlations below the threshold level are set to zero or another value. The position along the line or within the region of interest associated with a maximum correlation between images is identified as a displacement, indicating movement of the valve. The thresholded correlation values are weighted, such as reciprocally, by the corresponding displacements. A one dimensional morphology filter is applied. The kernel of the filter is set to a width relative to the widest or broadest range of non-zero correlations of the displacement-weighted correlations. For example, the kernel is 80% or other value of the broadest range. If a given consecutive set of non-zero correlations is less than the filter kernel in length, the correlations are set to zero. As a result, a single group of consecutive non-zero correlations is identified for each cycle. The single group corresponds to a closed valve and the zero regions correspond to an open valve. The change between correlations represents the closing and opening. Other approaches may be used.

Combinations of more than one approach with the same data may be used. Combinations of more than one approach with more than one respective type of data may be used. The algorithms discussed herein are examples, but other algorithms implemented by the processor 14 may be used. Other algorithms for other types of ultrasound or medical image data may be used. Opening and/or closing of one, two or more valves for the same or different heart cycles may be detected using the same or different data.

The processor 14 or another processor determines the timing of opening, closing or both opening and closing of a heart valve relative to a heart cycle. Cardiac event times are measured in reference to an ECG R-wave. The ECG wave is provided as input information with the images or derived by the processor 14 from ultrasound data variation. The ECG R-wave may be defined based on the peak slope, based on the peak value measured or other technique. Alternatively, other points in the heart cycle may be used. In yet other alternatives, other representations of the heart cycle are used.

In one embodiment, the processor 14 or another processor determines the timing for one or more cycles using the algorithm or algorithms as applied to ultrasound data and determines the timing for one or more other cycles by extrapolation or interpolation. For a given patient, the timing of the valve opening and closing relative to the heart cycle may be consistent. Given a measured length of a heart cycle, the timing of valve motion for that heart cycle is determined based on the length of another heart cycle and the identified timing of the cardiac event of the other heart cycle.

The processor 14 or another processor performs automatic ejection fraction, strain rate analysis, dyssynchrony analysis or combinations thereof as a function of the timing. A single valve time or a table of valve times is constructed. The times are exported to analysis programs. For example, for the left ventricle, the aortic valve opening and closing times and the mitral valve opening and closing times are used to define the onset and end of mechanical systole and the onset and end of diastolic filling. Both valves are closed during isovolumic contraction (i.e., just prior to aortic valve opening) and during isovolumic relaxation (i.e., just prior to mitral valve opening). For automatic ejection fraction analysis, the frames and/or volumes used in the analysis are selected as being immediately after the aortic and mitral closing times. For automatic strain rate analysis, various parameters such as the peak systolic strain rate, the time to the peak systolic strain rate, and the end systolic strain are extracted from the various intervals defined by the valve events. For automated dyssynchrony analysis, the analysis interval is determined by the valve events. Other automated or processor based applications may be used in addition or alternatively. For example, any now known or later developed computer assisted diagnosis software, hardware or system implements a diagnosis application using, at least in part, the cardiac event timing.

FIG. 2 shows a method for automated identification of a cardiac event. The method is implemented with the system 10 of FIG. 1 or a different system or systems. Fewer, different or additional acts than shown in FIG. 2 may be used. The acts may be performed in the same or different order.

In act 22, ultrasound data responsive to a heart valve is obtained. The data is obtained by scanning a patient with acoustic energy. The scan may be from outside a patient or inside the patient, such as from within an esophageus or circulatory system. Alternatively, the ultrasound data is obtained by transfer from storage, such as network transmission of the data from a database or delivery of a moveable storage media.

The ultrasound data includes one or more types of data. For example, B-mode images, an m-mode strip image, a spectral Doppler image, tissue velocity images, fluid velocity images, or combinations thereof are obtained. The ultrasound data may also have temporal markers relating each frame or time increment to a cardiac cycle. ECG or other cycle information may be provided with the ultrasound data.

In act 24, opening, closing or both opening and closing of the heart valve is identified with a processor as a function of the obtained ultrasound data. The processor identifies the heart valve motion without an indication of the heart valve motion by a user. The user may provide no input, initiate processing, provide one or more regions of interest, indicate a type of heart valve being analyzed, or refine cardiac event identification.

Different processing may be used to identify the heart valve opening and/or closing. For example, a correlation is determined between the B-mode images. Greater correlation may indicate a stationary or closed valve and lesser correlation may indicate a moving or open valve. Correlation with data representing the valve in a known state may alternatively be used. As another example, a pattern corresponding to the opening, closing or both opening and closing is identified in an M-mode strip image. As yet another example, an envelope is detected in a spectral Doppler image, and the locations where the envelope is closest to zero on either side of a peak in a positive or a negative portion of the envelope are identified as associated with opening and closing. Locations of minimum flow on either side of peaks in a positive or a negative portion of the envelope indicate the opening and closing. The use of the positive or negative portions depends on the valve being scanned and the direction of scanning. As another example, velocities from a region of interest associated with the heart valve are averaged as a function of time from tissue velocity images, and one or more notches near zero velocity in the average velocity is identified as a function of time.

In addition to the ultrasound data, other information may be used to identify the cardiac events. ECG or heart cycle signals may be used, such as to identify notches, peaks, minima, maxima or other features as a function of an R-wave or other cyclical event. Representative data, regions of interest, trained processes or combinations thereof may be used.

Based on the identified opening or closing events, the timing of the opening, closing or both opening and closing of the heart valve is determined in act 26. The timing is relative to a heart cycle, relative to other events or an absolute time. For example, the amount of time from a most recent R-wave is determined for each cardiac event. The timing and heart cycle information, such as the length of the heart cycle, are stored or provided for subsequent analysis.

Automatic ejection fraction, strain rate analysis, dyssynchrony analysis or combinations thereof are performed as a function of the timing. The timing is used to select data for analysis or as input to the analysis function.

The cardiac cycle may not be consistent from beat to beat. Irregularities in cardiac electrical events or in cardiac loading conditions which are affected by the respiratory cycle may cause variations in cardiac events from one heart cycle to the next. To reduce these effects, the measurement of cardiac events may be restricted to times when an R-R interval is very similar to the R-R interval of the previous heartbeat. Alternatively, additional timing information may be interpolated or extrapolated. The timing information is for a same or different patient. Timing measurements obtained from act 26 may be accumulated from one or more R-R intervals. For example, a look-up-table of expected event times as a function of the heart cycle lengths is created.

When an event time is required for a specific R-R interval, the value can be interpolated or extrapolated from the measured data. The timing is interpolated as a function of the heart cycle length relationship to two or more similar or closest heart cycle lengths. Alternatively, the timing is extrapolated as a function of the heart cycle length relationship to one or more similar or closest heart cycle lengths. The ratio of heart cycle lengths with measured times relative to the heart cycle length without a measured cardiac event time is determined. The ratio is applied to the known timing to derive the non-measured timing. The derived timing is used for diagnosis or performing an automated application, such as performing automatic ejection fraction, strain rate analysis, dyssynchrony analysis or combinations thereof.

The instructions for implementing the processes, methods, applications and/or techniques discussed above are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, filmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for automated identification of a cardiac event, the method comprising:
    obtaining ultrasound data responsive to a heart valve; and
    identifying, with a processor, an opening, closing or both opening and closing of the heart valve as a function of the ultrasound data;
    wherein the obtaining and the identifying comprise at least one of:
        (a) obtaining B-mode images and determining a correlation between the B-mode images as the opening or closing in the heart valve;
        (b) obtaining the spectral Doppler image and detecting an envelope and identifying locations of minimum flow on either side of peaks in a positive or a negative portion of the envelope; or
        (c) obtaining tissue velocity images and averaging velocities from a region of interest associated with the heart valve as a function of time and identifying one or more notches near zero velocity in the average velocity as a function of time.

2. The method of claim 1 wherein the obtaining comprises obtaining the B mode images and wherein the identifying comprises determining the change correlation between the B-mode images as the change in the heart valve.

3. The method of claim 1 wherein the obtaining comprises obtaining an M-mode strip image and wherein the identifying comprises identifying a pattern corresponding to the opening, closing or both opening and closing in the M-mode strip image.

4. The method of claim 1 wherein the obtaining comprises obtaining the spectral Doppler image and wherein the identifying comprises detecting the envelope and identifying the locations of minimum flow on either side of the peaks in the positive or the negative portion of the envelope.

5. The method of claim 1 wherein the obtaining comprises obtaining the tissue velocity images and wherein the identifying comprises averaging velocities from the region of interest associated with the heart valve as a function of time and identifying the one or more notches near zero velocity in the average velocity as a function of time.

6. The method of claim 5 wherein the identifying the one or more notches in (c) is a function of an R-wave event.

7. The method of claim 1 wherein the identifying is performed as a function of a user indication of an identity of the heart valve.

8. The method of claim 1 further comprising:
    determining a timing of the opening, closing or both opening and closing of the heart valve relative to a heart cycle.

9. The method of claim 8 further comprising:
    performing automatic ejection fraction, strain rate analysis, dyssynchrony analysis or combinations thereof as a function of the timing.

10. The method of claim 8 wherein the heart cycle has a first heart cycle length;
    further comprising:
    interpolating or extrapolating the timing as a function of the first heart cycle length relationship to another heart cycle length.

11. A system for automated identification of a cardiac event, the system comprising:
    a memory operable to store ultrasound data responsive to a heart valve; and
    a processor operable to identify heart valve motion with the ultrasound data;
    wherein the processor is operable to identify by determining a correlation or image pattern match between the ultrasound data as a function of time, wherein the correlation or image pattern match indicates the heart valve closing or opening.

12. The system of claim 11 wherein the ultrasound data comprises B-mode images, an M-mode strip image, a spectral Doppler image, tissue velocity images, fluid velocity images, or combinations thereof.

13. The system of claim 11 wherein the processor is operable to identify as a function of a parameter variation as a function of time.

14. The system of claim 11 wherein the processor is operable to identify as a function of a user indication of an identity of a heart valve.

15. The system of claim 11 wherein the processor is operable to determine a timing of an opening, closing or both opening and closing of a heart valve relative to a heart cycle.

16. The system of claim 15 wherein the processor is operable to perform automatic ejection fraction, strain rate analysis, dyssynchrony analysis or combinations thereof as a function of the timing.

17. The system of claim 15 wherein the heart cycle has a first heart cycle length, and wherein the processor is operable to interpolate or extrapolate the timing as a function of the first heart cycle length relationship to another heart cycle length.

* * * * *